(12) United States Patent
     Williams

(10) Patent No.: US 9,920,453 B2
(45) Date of Patent: *Mar. 20, 2018

(54) GENERATION OF LIBRARY OF SOLUBLE RANDOM POLYPEPTIDES LINKED TO MRNA

(71) Applicant: ProteoNova, Inc, Pasadena, CA (US)

(72) Inventor: Richard B Williams, South Pasadena, CA (US)

(73) Assignee: ProteoNova, Inc., Pasadena, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 14/741,265

(22) Filed: Jun. 16, 2015

(65) Prior Publication Data

US 2015/0353924 A1     Dec. 10, 2015

Related U.S. Application Data

(63) Continuation of application No. 12/525,437, filed as application No. PCT/US2008/053757 on Feb. 12, 2008, now Pat. No. 9,080,256.

(60) Provisional application No. 60/900,869, filed on Feb. 12, 2007.

(51) Int. Cl.

| | | |
|---|---|---|
| *C40B 50/06* | (2006.01) | |
| *C40B 40/02* | (2006.01) | |
| *C07K 14/00* | (2006.01) | |
| *C12N 15/10* | (2006.01) | |
| *C40B 10/00* | (2006.01) | |
| *C40B 40/08* | (2006.01) | |

(52) U.S. Cl.
    CPC ............ *C40B 40/02* (2013.01); *C07K 14/003* (2013.01); *C12N 15/1037* (2013.01); *C12N 15/1062* (2013.01); *C12N 15/1075* (2013.01); *C40B 10/00* (2013.01); *C40B 40/08* (2013.01); *C40B 50/06* (2013.01)

(58) Field of Classification Search
    None
    See application file for complete search history.

(56) References Cited

U.S. PATENT DOCUMENTS

| | | | |
|---|---|---|---|
| 4,599,303 | A | 7/1986 | Yabusaki et al. |
| 5,658,734 | A | 8/1997 | Brock et al. |
| 6,306,393 | B1 | 10/2001 | Goldenberg |
| 6,800,455 | B2 | 10/2004 | Stanton et al. |
| 7,560,110 | B2 | 7/2009 | Goldenberg et al. |
| 2002/0031762 | A1 | 3/2002 | Merryman et al. |
| 2004/0215400 | A1 | 10/2004 | Slovic et al. |

(Continued)

FOREIGN PATENT DOCUMENTS

| | | |
|---|---|---|
| EP | 1548111 | 6/2005 |
| WO | WO 98/31700 | 7/1998 |

(Continued)

OTHER PUBLICATIONS

Teare, J. & Wollenzien, P. Nucleic Acids Research. 1990, vol. 18(4), pp. 855-864.

(Continued)

*Primary Examiner* — Christian Boesen

(74) *Attorney, Agent, or Firm* — Knobbe Martens Olson & Bear LLP

(57) ABSTRACT

Methods and compositions are provided for producing libraries of soluble random polypeptides. In the methods, the fraction of hydrophilic residues in the polypeptide is controlled so as to maintain the solubility of the polypeptide constructs.

10 Claims, 2 Drawing Sheets

(56) References Cited

U.S. PATENT DOCUMENTS

2004/0265321 A1 12/2004 Johnson et al.
2006/0127893 A1 6/2006 Ewert et al.
2007/0015181 A1 1/2007 Williams

FOREIGN PATENT DOCUMENTS

| WO | WO 2001/07657 | 2/2001 |
| WO | WO 2001/90414 | 11/2001 |
| WO | WO 2003/044194 | 5/2003 |
| WO | WO 2004/048413 | 6/2004 |
| WO | WO 2005/047502 | 5/2005 |
| WO | WO 2005/072087 | 8/2005 |
| WO | WO 2006/076417 | 7/2006 |
| WO | WO 2010/051215 | 5/2010 |

OTHER PUBLICATIONS

Favre, A. et al. J. Photochem. and Photobiol. 1998, vol. 42, pp. 109-124.

Brown, C.M. & Tate, W.P. J. Biol. Chem. 1994, vol. 269(52), pp. 33164-33170.

Doi, et al., High solubility of random-sequence proteins consisting of five kinds of primitive amino acids; 2005, PEDS, vol. 18, pp. 279-284.

Keefe, et al. Functional proteins from a random-sequence library, Nature, vol. 410, pp. 715-718, Apr. 2001.

Takahashi, et al. mRNA display: ligand discovery, interaction analysis and beyond. Trends in Biochemical Sciences vol. 28, No. 3, Mar. 2000.

Cho, et al., Constructing High Complexity Synthetic Libraries of Long ORFs Using In Vitro Selection, J. Mol. Biol., vol. 297:309-319 (2000).

Prijambada, et al., Solubility of artificial proteins with random sequences, FEBS Letters, vol. 382:21-25 (1996).

Fukuda, et al., In vitro evolution of single-chain antibodies using mRNA display, Nucleic Acids Research, vol. 34(19): e127 (2006).

Yamauchi, et al., Characterization of soluble artificial proteins with random sequences, FEBS Letters, vol. 421:147-151 (1998).

Riddle, et al., Functional rapidly folding proteins from simplified amino acid sequences, Nature Structural Biol., vol. 4(10): 805-809 (1997).

Davidson et al., Cooperatively folded proteins in random sequence libraries, Nature Structural Biology, vol. 2 (10): 856-864 (1995).

Davidson et al., Folded proteins occur frequently in libraries of random amino acid sequences, PNAS, vol. 91:2146-2150 (1994).

Smialowski et al., Bioinformatics, vol. 23, pp. 2536-2542, Dec. 6, 2006.

GENERATION OF LIBRARY OF SOLUBLE RANDOM POLYPEPTIDES LINKED TO MRNA

CROSS-REFERENCE TO RELATED APPLICATIONS

This application is a continuation of co-pending U.S. application Ser. No. 12/535,437, filed Jul. 31, 2009, which is the U.S. national phase under 35 U.S.C. § 371 of PCT International Application No. PCT/US08/53757 which has an International Filing date of Feb. 12, 2008, and which claims priority to U.S. Provisional Application No. 60/900,869, filed Feb. 12, 2007. The priority applications are incorporated herein by reference in their entirety.

BACKGROUND OF THE INVENTION

Field of the Invention

The present invention relates to compositions and methods for producing libraries of soluble random polypeptides.

Description of the Related Art

In vitro evolution of proteins is a process in which a starting population of proteins, which may have desirable properties, is subjected to rounds of selection and mutation in order to evolve proteins having improved properties. For example, proteins can be selected for their binding properties to targets such as receptors. The proteins may be linked to their encoding polynucleotides as in RNA display, ribosome display, phage display etc., and after recovery of a subset of proteins having a desirable property, the polynucleotides encoding those proteins may be subjected to mutation in order to obtain a population of proteins for use in a further round of selection. In this way, proteins having better properties may be quickly obtained by evolution. Systems for accomplishing such in vitro evolution of proteins are disclosed, for example, in U.S. patent application Ser. No. 11/415,844, which is incorporated herein by reference in its entirety.

Often, when the proteins are attached to a large soluble entity, such as their mRNA, the entity acts as a solubility tag to keep the ensemble in solution. In such cases, when the protein is dissociated from the tag does it falls out of solution. Because the evolution step did not use a selection step or steps based on solubility, very little of the results may be usable. Thus, the construction of libraries of soluble protein constructs from which to make functional selections has become more important (*Eur. J. Biochem.* 271, 1595-1608; *FEBS* 2004). Libraries that lack a stop codon can be constructed, but they provide proteins that are not necessarily soluble. In one notable example, Cho et al. constructed a library and selected therefrom an ATP binding protein, bound to its mRNA. However, when separated from their bound mRNA, the proteins thus selected were highly insoluble. Cho, G., Keefe, A. D., Liu, R., Wilson, D. S., and Szostak, J. W. (2000) *J. Mol. Biol.* 297, 309-319, which is incorporated herein by reference in its entirety. Only a fraction of each clone appeared folded and functional; the proteins themselves tend to aggregate when expressed as free proteins. It has been hypothesized that selection of these proteins was likely facilitated by the improved solubility imparted by the mRNA-cDNA tail, which indicates such sequences would not be found in a typical phage-display selection. Takahashi, T. et al., *TRENDS in Biochemical Sciences*, Vol. 28, No. 3, March 2003, which is incorporated herein by reference in its entirety. The method described by Cho et al. employed a 109 amino acid construct, of which 80 amino acids were random. Cho, G., Keefe, A. D., Liu, R., Wilson, D. S., and Szostak, J. W. (2000) J. Mol. Biol. 297, 309-319. The Cho et al. method did not involve biasing the codons. The 29 amino acids at the construct ends were not identified, but unless they were markedly biased one could not expect this population to be soluble, on average.

It has been suggested that the insolubility of functional clones likely reflects the relative paucity of proteins that are both folded and functional in the vastness of sequence space. Takahashi, T. et al., *TRENDS in Biochemical Sciences*, Vol. 28, No. 3, March 2003. Thus, there is a need for methods for the preparation of soluble proteins, and libraries of soluble proteins.

SUMMARY OF THE INVENTION

In one embodiment, a method of producing a library of soluble polypeptides linked to polynucleotides encoding the polypeptides is provided that comprises: synthesizing a plurality of polynucleotides; producing encoded polypeptides from the polynucleotides; and linking each polypeptide to the polynucleotide that encodes it; wherein a proportion of hydrophilic or surface compatible amino acid residues in each polypeptide is selected so that the polypeptide will be soluble.

In a further embodiment, the polypeptides can be approximately 100 amino acid residues in length. In a further embodiment, the polynucleotides can be synthesized using uncapped trimer phosphoramidites. In a further embodiment, the polynucleotides do not contain stop codons.

In a further embodiment, the hydrophilic or surface compatible amino acid residues can be selected from the group consisting of Asp, Arg, Ser, Gln, Asn, Lys, Glu, Gly, Pro, and combinations thereof. In a further embodiment, the hydrophilic or surface compatible amino acid residues can be selected from the group consisting of Arg, Lys, Asn, His, Pro and Asp and combinations thereof. In a further embodiment, at least one proline or glycine residue can be included each polypeptide.

In a further embodiment, the proportion of hydrophilic or surface compatible amino acid residues in each polypeptide can be selected using the following formula:

$$c = \left(\frac{8}{0.41N}\right)^{\frac{1}{3}} \pm y$$

where N=the number of amino acids in molecule, c=fraction of amino acids that are hydrophilic or surface compatible, and y is selected from the group consisting of 0.01, 0.02, 0.03, 0.04 and 0.05.

In a further embodiment, the proportion of hydrophilic or surface compatible amino acid residues in each polypeptide can be selected using the following formula:

$$c \geq \left(\frac{8}{0.41N}\right)^{\frac{1}{3}} - 0.05$$

wherein N=the number of amino acids in each polypeptide, and c=fraction of amino acids that are hydrophilic.

In a further embodiment, the proportion of hydrophilic or surface compatible amino acid residues in each polypeptide can be selected using the following formula:

$$c = \left(\frac{8}{0.41N}\right)^{\frac{1}{3}} \pm 0.05$$

wherein N=the number of amino acids in each polypeptide, and c=fraction of amino acids that are hydrophilic.

In one embodiment, a library of soluble polypeptides linked to polynucleotides encoding the polypeptides is provided that comprises: a library of soluble polypeptides linked to polynucleotides encoding the polypeptides produced by a method that comprises: synthesizing a plurality of polynucleotides; producing encoded polypeptides from the polynucleotides; and linking each polypeptide to the polynucleotide that encodes it; wherein a proportion of hydrophilic or surface compatible amino acid residues in each polypeptide is selected so that the polypeptide will be soluble.

In a further embodiment, the library can be a phage library. In a further embodiment, the library of claim can reside within a eukaryotic cell. In a further embodiment, the library can be a ribosome display library. In a further embodiment, the library can be an RNA display library. In a further embodiment, the library can be a plasmid display library. In a further embodiment, the polynucleotides do not contain stop codons.

DETAILED DESCRIPTION OF THE PREFERRED EMBODIMENT

Figure 1:
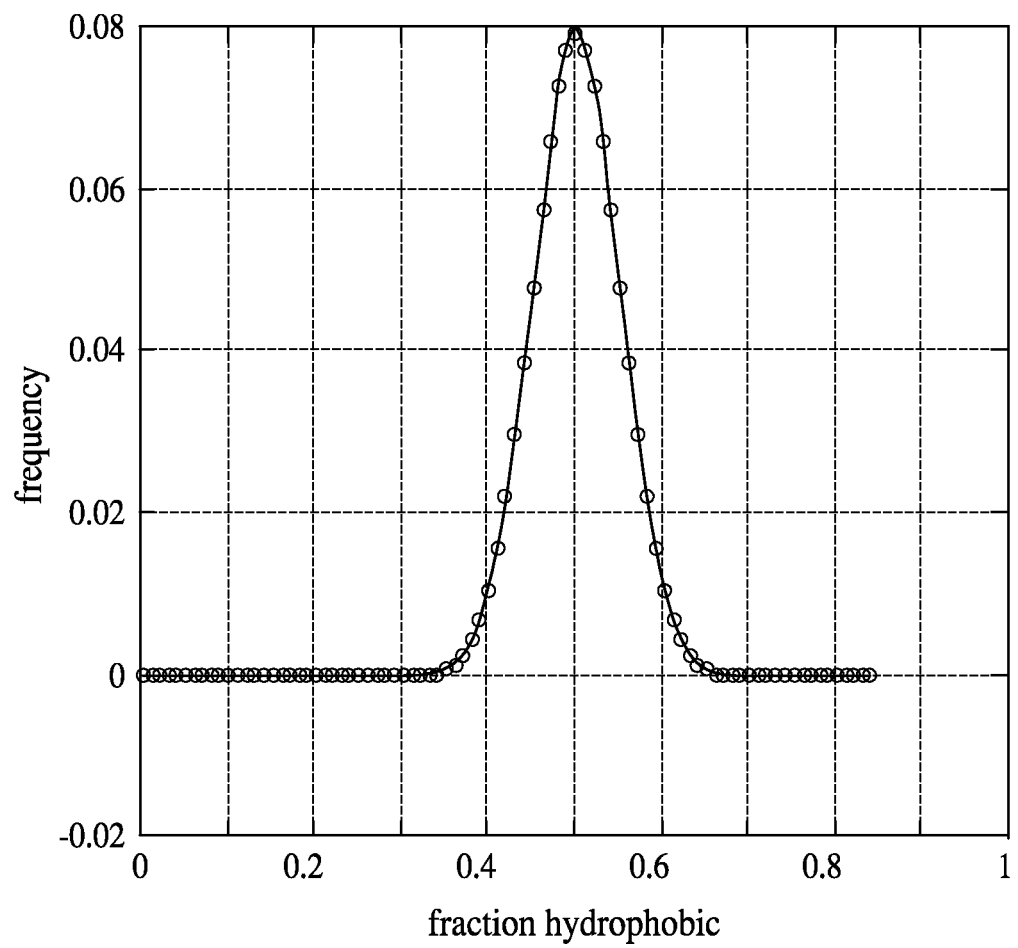
FIG. 1 depicts the distribution of a population of proteins 100 amino acids in length by hydrophobic amino acid fraction. If the sequences are selected from a population of 50% hydrophilic and 50% hydrophobic amino acids which is roughly the ratio of the 61 sense codons. From Min-yi Shen, Fred P. Davis, Andrej Sali; The optimal size of a globular protein domain: A simple sphere-packing model; *Chemical Physics Letters* 405 (2005) 224-228).

The present disclosure relates to compositions and methods to generate libraries of random polypeptides which are intrinsically soluble. In various embodiments, methods for preparing libraries of soluble proteins are provided. Advantageously, the libraries disclosed herein can be in a variety of different formats, including RNA display, ribosome display, phage display etc. Some embodiments described herein relate to preparation of soluble polypeptides the by controlling the ratio of hydrophilic to hydrophobic amino acids present in the polypeptides. Some embodiments described herein relate to preparation of soluble polypeptides the by controlling the content of surface compatible amino acids in the polypeptides. In various embodiments disclosed herein, methods are provided for the selection of a soluble product of in vitro evolution. Various embodiments described herein relate to preparation of soluble polypeptides linked to polynucleotides encoding the polypeptides.

As will be appreciated by one of skill in the art, the ability to make soluble polypeptides can have great benefit in a wide variety of applications, including, for example, increasing accessibility to selection systems. The methods disclosed herein, and libraries generated by such methods, are useful, for example, in in vitro evolution processes to develop polypeptides that have desirable properties. Such properties include, for example, enhanced binding to a target protein, such as a receptor, or the development of polypeptides for use in vaccines.

The above and additional embodiments are discussed in mote detail below, after a brief discussion of the definitions some of the terms used in the specification.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. As utilized in accordance with the embodiments provided herein, the following terms, unless otherwise indicated, shall be understood to have the following meanings:

The terms "protein," "peptide," and "polypeptide" are defined herein to mean a polymeric molecule of two or more units comprised of amino acids in any form (e.g., D- or L-amino acids, synthetic or modified amino acids capable of polymerizing via peptide bonds, etc.), and these terms may be used interchangeably herein.

The term "linked" as used herein means associated. Linked entities as described herein can be, but need not be, directly physically connected to each other. In some embodiments, linked entities are directly physically attached to each other. One example of a direct physical linkage is a polypeptide-mRNA fusion. Another example of a direct physical linkage is a ribosome linking an mRNA to the polypeptide synthesized from the mRNA. In other embodiments, entities can be indirectly linked by association with the same phage, ribosome, or cell, but are not necessarily directly physically attached to each other. Examples of indirect linkages include, without limitation: a phage containing a polynucleotide and expressing the polypeptide encoded by the polynucleotide, and a cell containing a polynucleotide and expressing the polypeptide encoded by the polynucleotide.

The term "surface compatible" as used herein means capable of existing on a surface of a polypeptide without substantially contributing to insolubility of the polypeptide. The amino acids Asp, Arg, Ser, Gln, Asn, Lys, Glu, Gly and Pro are considered "surface compatible."

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. .alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "nucleic acid" refers to natural nucleic acids, artificial nucleic acids, analogs thereof, or combinations thereof.

As used herein, the terms "polynucleotide" and "oligonucleotide" are used interchangeably and mean single-stranded and double-stranded polymers of nucleotide monomers (nucleic acids), including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

The term "tRNA molecule", as used herein, shall be given its ordinary meaning and shall also mean a stable aminoacyl tRNA analog (SATA), a Linking tRNA Analog, and a Nonsense Suppressor Analog, all of which are described herein. A tRNA molecule includes native tRNA, synthetic tRNA, a combination of native and synthetic tRNA, and any modifications thereof. In a preferred embodiment, the tRNA is connected to the nascent peptide by the ribosomal peptidyl transferase and to the mRNA through an ultraviolet induced crosslink between the anticodon of the tRNA molecule and the codon of the RNA message. This can be done by, for example, thiouracil, bromouracil, and the like. In one preferred embodiment, the linker is a psoralen crosslink made from a psoralen monoadduct, a non-psoralen crosslinker, or analogs or modifications thereof, pre-placed on either the mRNA's last translatable codon or preferably on the tRNA anticodon of choice. Preferably, a tRNA stop anticodon is selected. A stop codon/anticodon pair selects for full length transcripts. One skilled in the art will understand that an mRNA not having a stop codon may also be used and, further, that any codon or nucleic acid triplet may be used in accordance with several embodiments of the current invention. A tRNA having an anticodon which is not naturally occurring can be synthesized according to methods known in the art.

In one embodiment, the anticodon of the tRNA is capable of forming a crosslink to the mRNA, where the cross-link is selected from the group consisting of one or more of the following: 2-thiocytosine, 2-thiouridine, 4-thiouridine 5-iodocytosine, 5-iodouridine, 5-bromouridine and 2-chloroadenosine, aryl azides, and modifications or analogues thereof. These crosslinkers are available commercially from Ambion, Inc. (Austin, Tex.), Dharmacon, Inc. (Lafayette, Colo.), and other well-known manufacturers of scientific materials.

The term "pseudo stop codon" is defined herein to mean a codon which, while not naturally a nonsense codon, prevents a message from being further translated. A pseudo stop codon may be created by using a "stable aminoacyl tRNA analog" or SATA, as described below. In this manner, a pseudo stop codon is a codon which is recognized by and binds to a SATA. Another method by which to create a pseudo stop codon is to create an artificial system in which the necessary tRNA having an anticodon complementary to the pseudocodon is substantially depleted. Accordingly, translation will stop when the absent tRNA is required, e.g., at the pseudo stop codon.

Selection of Amino Acids for Soluble Polypeptides

Many uses for polypeptides require aqueous solubility. Using the methods disclosed herein, one can construct libraries that are biased to produce soluble polypeptides.

Solubility of a polypeptide is dependent on, among other protein characteristics, the proportion of hydrophobic residues therein and the length of the polypeptide. Generally, for a polypeptide to be soluble, the polypeptide preferably has an adequate number of hydrophilic amino acids available to coat the hydrophobic core, regardless of any folding constraints. Since the surface to volume ratio of a molecule increases with decreasing size, this ratio will differ for different sizes or lengths of sequences.

A simple model shows that for unbiased amino acid content, the optimal size for solubility is ~150 amino acids. Shen, M.-Y., Davis, F., Sali, A. Chemical Physics Letters (2005) 405, pp. 224-228, which is incorporated herein by reference in its entirety. According to this simple model, 2005, at least 90% of polypeptides 109 amino acids long would be expected to be insoluble. If amino acids are considered as hydrophobic versus hydrophilic, or surface versus core occupiers, the distribution of different ratios in a population can be seen as a binomial with the percentages of the two types as the probabilities p and 1−p:

$$\frac{n!}{r!(n-r)!}p^r(1-p)^{n-r}$$

where r is the number of amino acids representing the first class present in a sequence and (n−r) representing the second class, with n=the length of the sequence. Thus, for a protein population having 50% hydrophobic and 50% hydrophilic amino acids, the population distribution by hydrophobic amino acid fraction for n=100 would look like that shown in FIG. 1.

One of the primary factors affecting polypeptide solubility is the exposure of hydrophobic amino acids to water solvent. For increased solubility, it is generally desirable for polypeptides to have their hydrophobic amino acids situated away from the water solvent. This is, in a way, a constraint of surface to volume ratio. The smaller the polypeptide, the greater the surface to volume ratio will be. Because surface to volume ratio changes with protein length, the proportion of hydrophilic to hydrophobic amino acids can be adjusted according to the number of total amino acids in the polypeptide to bias the ratio towards solubility.

For a completely hydrophilic amino acid polypeptide population, there will be no structure because the molecules will be able to completely unfold. When this is compared to a population with a very low but nonzero hydrophobic amino acid fraction, the hydrophilic amino acid residues have fewer ways to distribute themselves and still shield the hydrophobic amino acid residues from the solvent. As the hydrophobic amino acid fraction of the polypeptide increases, the constraints on the positioning of hydrophilic amino acid residues increase, thus leading to a greater tendency towards structure. This tendency progresses next to "random coils" then to "intrinsically disordered polypeptides" then to "molten globules" and rigid, highly structured globules and finally to insoluble aggregates. Thus, as the hydrophobic amino acid population of a polypeptide increases from zero to 100%, the structure of the polypeptide changes as follows: no structure→random coils→intrinsically disordered polypeptides→molten globules→rigid, highly structured globules→insoluble aggregates.

Generally, for a given length of polypeptide, there will be a hydrophilic to hydrophobic ratio that is optimal for intrinsically disordered polypeptides, a lower hydrophilic to hydrophobic ratio for ratio for molten globules yet a lower one, and an even lower hydrophilic to hydrophobic ratio for rigid globules below which there is little chance of solubility.

In preparing soluble polypeptide libraries, the distribution of hydrophobic and hydrophilic or surface compatible amino acid residues in the polypeptides can be selected to bias content towards solubility by selecting the proportion of amino acids that are hydrophilic or surface compatible so that the polypeptides will be soluble. The following formula can be used to select the proportion of amino acids that are hydrophilic or surface compatible so that the polypeptides will be soluble:

$$c = \left(\frac{8}{0.41N}\right)^{\frac{1}{3}}$$

where N=the number of amino acids in the polypeptide and c=fraction of amino acids that are hydrophilic or surface compatible. This formula is derived as follows:

$$N = \frac{8}{0.41c^3}$$

$$c^3 = \frac{8}{0.41N}$$

$$c = \left(\frac{8}{0.41N}\right)^{\frac{1}{3}}$$

where N=the number of amino acids in the polypeptide, and c=fraction of amino acids that are hydrophilic or surface compatible. In one example using the above formula, for N=100, the proportion of the surface compatible amino acids would be 58% and the interior 42%. Using the above formula as a guideline for selecting the proportion of amino acids that are hydrophilic or surface compatible, the adjustment of the distribution of hydrophobic and hydrophilic, or "surface compatible" amino acid residues in the polypeptides can be performed until a desired level of solubility is achieved.

The amino acids Asp, Arg, Ser, Gln, Asn, Lys, Glu, Gly and Pro are considered "surface compatible." In addition to selecting the proportion of amino acids that are hydrophilic or surface compatible, sharp turns in the backbone for amino acids will also help with solubility, especially as the polypeptide gets smaller. Thus, in some embodiments, the addition of glycine and proline can also be included in the bias. In some embodiments involving simple binding polypeptides, a loose polypeptide configuration with high solubility can often be adequate. Thus, in such situations where loose polypeptide configurations and high solubility are sufficient, fewer mutation steps are required. In other embodiments requiring a tighter, more rigid polypeptide structure it can be useful to go more toward the limit of solubility. In other words, in some embodiments, it can be desirable to adjust the distribution of hydrophobic and hydrophilic amino acid residues in the polypeptides such that the polypeptide is nearly insoluble. This can be done by, for example, starting closer to the limit of solubility or by continuing to mutate additional times.

It is estimated that each mutation step changes the proportion of hydrophilic and hydrophobic amino acids in a polypeptide toward the mean of the random codon triplets about 1.5% if the sequences are selected from a population of 50% hydrophilic and 50% hydrophobic amino acids, which is roughly the ratio of the 61 sense codons. This assumes a mutation rate of one mutation for each sequence on average. Different rates would give different changes in the proportion.

In some embodiments, the following formula can be used to select the proportion of amino acids that are hydrophilic or surface compatible so that the polypeptides will be soluble:

$$c = \left(\frac{8}{0.41N}\right)^{\frac{1}{3}} \pm y$$

where N=the number of amino acids in molecule, c=fraction of amino acids that are hydrophilic or surface compatible, and y can be about 0, 0.01, 0.02, 0.03, 0.04 or 0.05.

In preferred embodiments, the following formula can be used to select the proportion of amino acids that are hydrophilic or surface compatible so that the polypeptides will be soluble:

$$c \geq \left(\frac{8}{0.41N}\right)^{\frac{1}{3}} - 0.05$$

where N=the number of amino acids in molecule, and c=fraction of amino acids that are hydrophilic or surface compatible.

In other preferred embodiments, the following formula can be used to select the proportion of amino acids that are hydrophilic or surface compatible so that the polypeptides will be soluble:

$$c = \left(\frac{8}{0.41N}\right)^{\frac{1}{3}} \pm 0.05$$

where N=the number of amino acids in molecule, and c=fraction of amino acids that are hydrophilic or surface compatible.

When the combined fraction of the surface compatible amino acids is much greater than c, the polypeptide population will be less rigid on average and have fewer constraints on its configuration. As combined fraction of the hydrophilic or surface compatible amino acids approaches c, the polypeptide will become more rigid and have fewer ways to fold.

Figure 2:
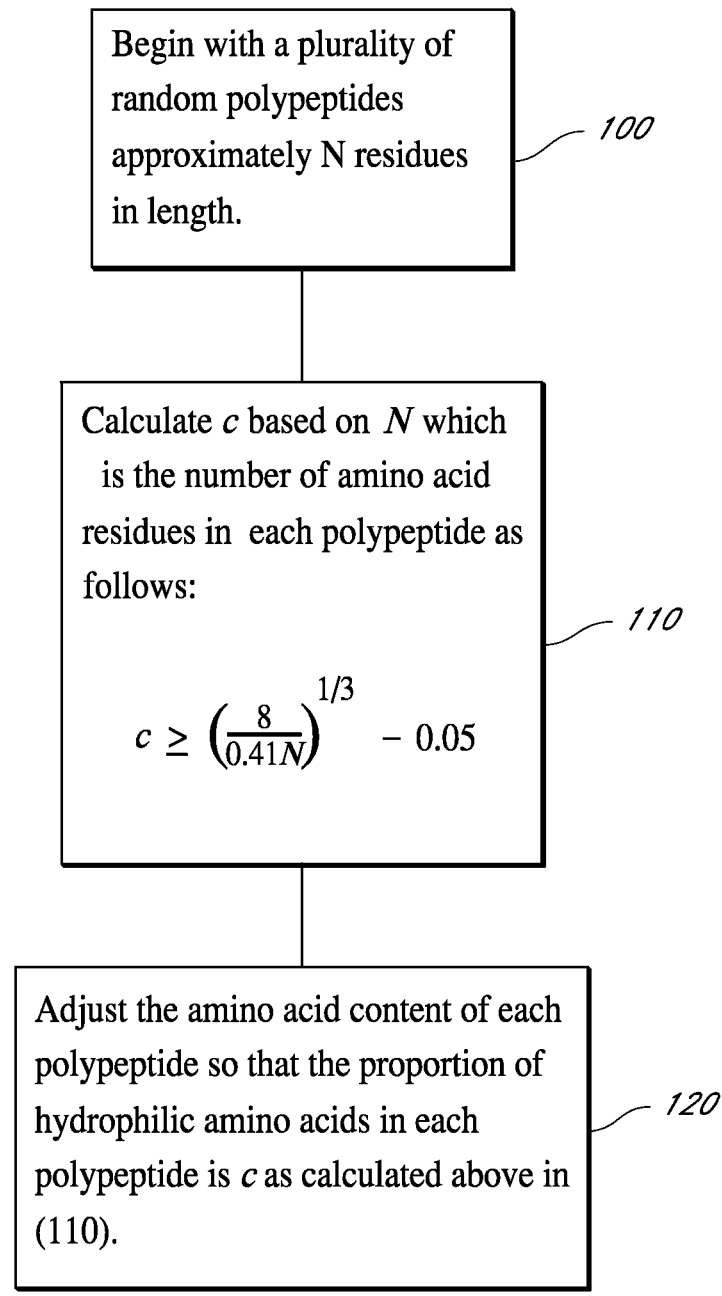
FIG. 2 depicts a flow chart describing various possible steps that can be taken during some of the disclosed embodiments.

FIG. 2. illustrates one embodiment for preparing libraries of soluble polypeptides. A plurality of random polypeptides approximately N residues in length can be used as a starting point (FIG. 2 at 100). N can be any number of amino acid residues, such as, for example without limitation, any number from about 2 to about 10,000 amino acids. In some embodiments, N can be about from about 10 to about 1000 amino acids. In other embodiments, N can be about from about 50 to about 500 amino acids. In other embodiments, N can be about from about 80 to about 150 amino acids. In other embodiments, N can be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120. A proportion c can be calculated based on N which is the number of amino acid residues in each polypeptide as follows:

$$c \geq \left(\frac{8}{0.41N}\right)^{\frac{1}{3}} - 0.05$$

where N=the number of amino acids in each polypeptide (FIG. 2 at 110). The new proportion of hydrophilic or surface compatible amino acids for each polypeptide is chosen to be c as calculated above for each polypeptide. The amino acid content of each polypeptide is adjusted so that the proportion of hydrophilic or surface compatible amino acids in each polypeptide is c as calculated above in (110), thereby providing a library of soluble polypeptides (FIG. 2 at 120).

Thus, soluble polypeptides can be designed by selecting the fraction of amino acids that are hydrophilic or surface compatible. Once the amino acid content of the polypeptides is selected, polynucleotides encoding the polypeptides can be synthesized using a variety of methods known in the art. Preferred embodiments for preparation of polynucleotides are described in the next section. Other exemplary methods suitable for preparing the soluble polypeptides designed as described herein are provided in, without limitation, Doi, N. et al., *Protein Engineering, Design & Selection* vol. 18 no. 6 pp. 279-284, 2005; Keefe, A. D. and Szostak, J. W. (2001) *Nature*, 410, 715-718; Yamauchi, A. et al. (1998) *FEBS Lett.*, 421, 147-151; Prijambada, I. et al. (1996) *FEBS Lett.*, 382, 21-25; and Davidson, A. and Sauer, R. (1994) *Proc. Natl Acad. Sci. USA*, 91, 2146-2150, all of which are incorporated herein by reference in their entireties. In some embodiments, the polynucleotides encoding soluble polypeptides can then be used, for example, to prepare libraries of soluble polypeptide linked to polynucleotides.

Polynucleotide Preparation

In some embodiments, polynucleotides encoding soluble polypeptides are prepared using nucleotide triplets that correspond to the codons for the amino acids desired. Synthesis of the polynucleotides can be carried out using a variety of methods known in the art. For example, polynucleotides can be prepared using methods employing phosphoramidites, other chemical methods for constructing 3' to 5' polynucleotides, or enzymatically using trinucleotides and a suitable ligase, such as, for example, T4 DNA or RNA ligase. In some embodiments, phosphoramidite methods can be used to construct short sequences which can be enzymatically ligated to the desired length.

In various embodiments, phosphoramidite technology can be used to make full length polynucleotides. In some embodiments, it can be useful to use a CPG support that has a pore size greater than, for example, about 1000 Å which accommodates synthesis of oligos longer than about 150 nucleotides. Such CPG supports are commercially available (for example, Millipore and 3-Prime for 3000 Å, Glen Research for 2000 Å). There are various ways known in the art to add the trinucleotides together.

In some embodiments, polynucleotides can be prepared using modified phosphoramidite systems. For example, polynucleotides can be prepared using modified phosphoramidites such as codon phosphoramidites, or nucleotide trimers that are fully protected for use in DNA synthesizers (commercially available at, for example, Biolytics). By mixing the trimers in the desired hydrophobic/hydrophilic ratio, one can simply add from a reservoir with this ratio repeatedly during the synthesis of the random portion of the sequence.

The coupling efficiency of the trimer phosphoramidites is generally only 80-90%, compared to the >99% for most phosphoramidite reagents. Capping with acetic anhydride can be used to prevent reading frame changes. However, if each sequence that fails to accept an addition is capped with acetic anhydride to remove it from further reactions, attrition can severely limit the length of many reagents. Thus, trimers used with conventional synthesis protocols tend to be very short. However, omitting the capping step without changing the reading frame can provide longer reagents. By replacing the capping step with a step that leaves the 5' ends open to further addition, further additions can be possible without any attrition. Because some protocols use capping for other functions such as drying (see, for example, the Expedite 8900 Workstation Software User's Guide) and rectification of side chain modifications (Pon, R. et al. (1986) *Nuc. Acids Res.* 14, 6453-6470), additional procedures may be desirable when omitting the capping step.

Deletion of the capping step can result in a distribution of uncapped additional lengths, instead of a single length. Since this will also follow a binomial with the added vs. non-added with a probability (assuming 80% coupling efficiency) of 0.8 and 0.2 respectively one would need to run 125 addition cycles to have an average of 100 random additions.

In some embodiment, a "mock" capping step with methylimidizole and an aqueous step but no acetic anhydride capping reagent can be used to construct a library of random nucleotides (Pon, R. T., Usman, N., Damha, M., and Ogilvie, K. K. (1986) *Nuc. Acids Res.* 14, 6453-6470; J. Scott Eadie and D. Scott Davidson, *Nucleic Acids Research* 15:8333-8349 1987) An aqueous step is used because the added phosphoramidite can attach to the 06 of guanine bases which later can lead to strand scission. The "mock" capping step or an aqueous step removes the modification from the guanine and prevents the scission.

In some embodiments, the polynucleotides do not include stop codons in the intended reading frame.

In various embodiments, the polynucleotides encoding soluble polypeptides can be used in to prepare libraries of soluble polypeptide linked to polynucleotides. The soluble polypeptides can be linked to the polynucleotides encoding them by, for example without limitation, RNA display, ribosome display, phage display, etc. A variety of library formats can be used to for the soluble peptide libraries.

Library Preparation

The libraries of the present invention can be prepared in a number of formats, including those described below. For each of the library formats, polynucleotides encoding the soluble polypeptides can be used can be used in preparing the soluble polypeptide libraries. The polynucleotides can be synthesized as described in the previous section, or by a variety of methods known in the art.

In some embodiments, libraries of soluble random polypeptides lacking stop codons that are linked to the mRNAs encoding those polypeptides are provided. In some embodiments, selection can be carried out on these polypeptide-mRNA fusions after dissociation of the ribosome. The methods disclosed in, for example, U.S. patent application Ser. No. 11/415,844 (which is incorporated herein by reference in its entirety) can be employed to produce polypeptide-mRNA fusions. In some embodiments, for example, a Linking tRNA Analog can be used to connect the mRNA to its cognate peptide. In some embodiments, the Linking tRNA Analog can be, for example, a native or a synthetic tRNA (or a combination of native-synthetic hybrid) that has a crosslinker positioned on the anticodon loop. Preferably, the crosslinker is bound to the anticodon loop through covalent bonding. In some embodiments, the Linking tRNA Analog accepts the nascent peptide onto its 3' aminoacyl moiety through the action of ribosomal peptidyl transferase. The 3' aminoacyl moiety can be native to the tRNA or can be synthetically introduced. In some embodiments, the ester bond between the peptide and the tRNA is protected from ribosomal peptidyl transferase because the message is untranslatable beyond the codon bound by the tRNA (the linking codon). Thus, the ribosomal peptidyl transferase will be unable to release the peptide from the tRNA. Therefore, in several embodiments of the present invention, the ester bond between the tRNA and a peptide chain is rugged enough to obviate the need for puromycin. The connection between the Linking tRNA Analog and the peptide, when linked through an ester bond, is protected from dissolution by ribosomal peptidyl transferase by making the translated message "untranslatable" beyond the linking codon. Advantageously, the message then will be stably attached to its peptide for further identification, selection and evolution. Another advantage is that synthetic or modified tRNAs need not be used in some embodiments employing the Linking tRNA Analog.

In some particular embodiments, the tRNA is unmodified in the sense that it is unmodified on the 3' end, and may or may not have minor modifications on the anticodon loop. In many embodiments, unmodified native tRNA (particularly unmodified on the 3' end) can be used, therefore making the system, among other things, more cost-effective, efficient, quicker, less error-prone, and capable of producing a much higher yield. Not wishing to be bound by the following theory, the presence of puromycin (or similar linkers) can result, in some cases, in low yield because puromycin obstructs the interaction of the elongation factor with tRNA thus affecting yield. Further, the elongation factor, when unobstructed by puromycin (or similar linkers) is able to accomplish dynamic proof-reading, thereby reducing error rates.

In addition to the RNA display library format described above, a number of cell-based library methods are available for the soluble polypeptide libraries, such as on the surfaces of phages (Smith, G. P. (1985) Science 228 1315-1317), bacteria (Georgiou, G., et. al. (1993) TIBTECH 11 6-10.) and animal viruses (Kasahara, N et al. (1994) Science 266, 1373-1376). In phage display, proteins or peptides are expressed individually on the surface of phage as fusions to a coat protein, while the same phage particle carries the DNA encoding the protein or peptide. Selection of the phage is achieved through a specific binding reaction involving recognition of the protein or peptide, enabling the particular phage to be isolated and cloned and the DNA for the protein or peptide to be recovered and propagated or expressed.

Another suitable library format for the soluble protein libraries disclosed herein is ribosome display. This format involves the display of polypeptides in nascent form on the surface of ribosomes, such that a stable complex with the encoding mRNA is also formed; the complexes are selected with a ligand for the protein or peptide and the genetic information obtained by reverse transcription of the isolated mRNA. This is known as ribosome or polysome display. A description of such a method can be found in two U.S. patents, granted to G. Kawasaki/Optein Inc. (Kawasaki, G., U.S. Pat. No. 5,643,768 Cell free synthesis and isolation of novel genes and polypeptides (Jul. 1, 1997) and U.S. Pat. No. 5,658,754 (Aug. 19, 1997), incorporated herein by reference in their entireties.)

The various devices and systems described above provide a number of ways to carry out the invention. It is to be understood that not necessarily all objectives or advantages described can be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A method of producing a library of soluble polypeptides linked to polynucleotides encoding the polypeptides, comprising:

synthesizing a plurality of polynucleotides wherein the sequence of each of the polynucleotides encodes a polypeptide, in a reading frame within which there is no stop codon, said reading frame comprising codons which are any one of the 61 sense codons, each of the encoded polypeptides having a proportion of hydrophilic or surface compatible amino acids such that:

$$c \geq \left(\frac{8}{0.41N}\right)^{\frac{1}{3}} - 0.05$$

wherein N is the number of amino acids in each polypeptide, wherein N≥17, and c is the fraction of amino acids that are hydrophilic or surface compatible, wherein said hydrophilic or surface compatible amino acid residues are Asp, Arg, Ser, Gln, Asn, Lys, Glu, Gly, Pro, His, or any combination thereof;

producing encoded polypeptides from the polynucleotides; and linking each polypeptide to the polynucleotide that encodes it, thereby producing said library of soluble polypeptides.

2. The method of claim 1, wherein said polynucleotides are synthesized using uncapped trimer phosphoramidites.

3. The method of claim 1, wherein the hydrophilic or surface compatible amino acid residues are Arg, Lys, Asn, His, Pro, Asp, or any combination thereof.

4. The method of claim 1, wherein said polypeptides contain at least one proline or glycine residue.

5. The method of claim 1, wherein 17≤N≤1000.

6. The method of claim 1, wherein N≥50.

7. The method of claim 6, wherein N≤10,000.

8. The method of claim 1, wherein N is 95, 96, 97, 98, 99, 100, 101, 102, 103, 104, or 105.

9. The library of claim 1, which resides in a eukaryotic cell.

10. The library of claim 1, which is an RNA display library.

* * * * *